United States Patent [19]

Holbrook et al.

[11] 3,938,540
[45] Feb. 17, 1976

[54] VACUUM-OPERATED FLUID BOTTLE FOR TANDEM SYSTEMS

[75] Inventors: Legrand K. Holbrook; David S. Ostler, both of Salt Lake City, Utah

[73] Assignee: Medical Development Corporation, Salt Lake City, Utah

[22] Filed: Oct. 2, 1973

[21] Appl. No.: 402,788

Related U.S. Application Data

[63] Continuation of Ser. No. 187,275, Oct. 7, 1971, abandoned, which is a continuation-in-part of Ser. No. 876,438, Nov. 13, 1969, Pat. No. 3,620,408.

[52] U.S. Cl. ............................... 137/205; 128/276
[51] Int. Cl.² .......................................... A61M 1/00
[58] Field of Search ...... 137/202, 205, 433; 141/42, 141/43; 128/276, 278

[56] References Cited
UNITED STATES PATENTS

| | | | |
|---|---|---|---|
| 1,153,660 | 9/1915 | Weinberg | 137/205 |
| 1,225,885 | 5/1917 | Stevens | 137/433 X |
| 1,519,826 | 12/1924 | Fuge | 137/205 |
| 1,535,541 | 4/1925 | Noble | 137/205 |
| 1,557,089 | 10/1925 | Reasoner | 137/433 |
| 1,656,124 | 1/1928 | Melotte | 137/205 X |
| 1,661,608 | 3/1928 | Grauel | 137/205 |
| 1,666,492 | 4/1928 | Gentile | 137/205 X |
| 1,793,159 | 2/1931 | Costa et al. | 141/43 |
| 2,037,467 | 4/1936 | Hapgood | 137/205 X |
| 2,317,589 | 4/1943 | Collinson | 137/205 X |
| 3,455,346 | 7/1969 | Stork | 141/42 |
| 3,620,408 | 11/1971 | Holbrook et al. | 220/44 R X |

*Primary Examiner*—Alan Cohan
*Assistant Examiner*—Gerald A. Michalsky

[57] ABSTRACT

The present invention comprises a vacuum-operated fluid-collection bottle and system including a serially connected tandem system. Dual vacuum bosses for a representative bottle, one being valved, in multiple-boss covers may be used as respective automatic shut-off and tandem-fill means, with the non-applicable boss being releasably capped off. Two of the three conduit portions of the cover may be connected together through appropriate valving system so that either or both may be effective in supplying vacuum communication to the interior of the bottle at selected height levels. Valving means pre-determine maximum fluid height within the bottle, either automatically or by valve adjustment. A representative bottle may include fluid inlet and vacuum ports of differing level-dimension, to aid the lower vacuum port to close off or to conduct outwardly body-fluid while maintaining the inlet port above the bottle fluid level.

3 Claims, 9 Drawing Figures

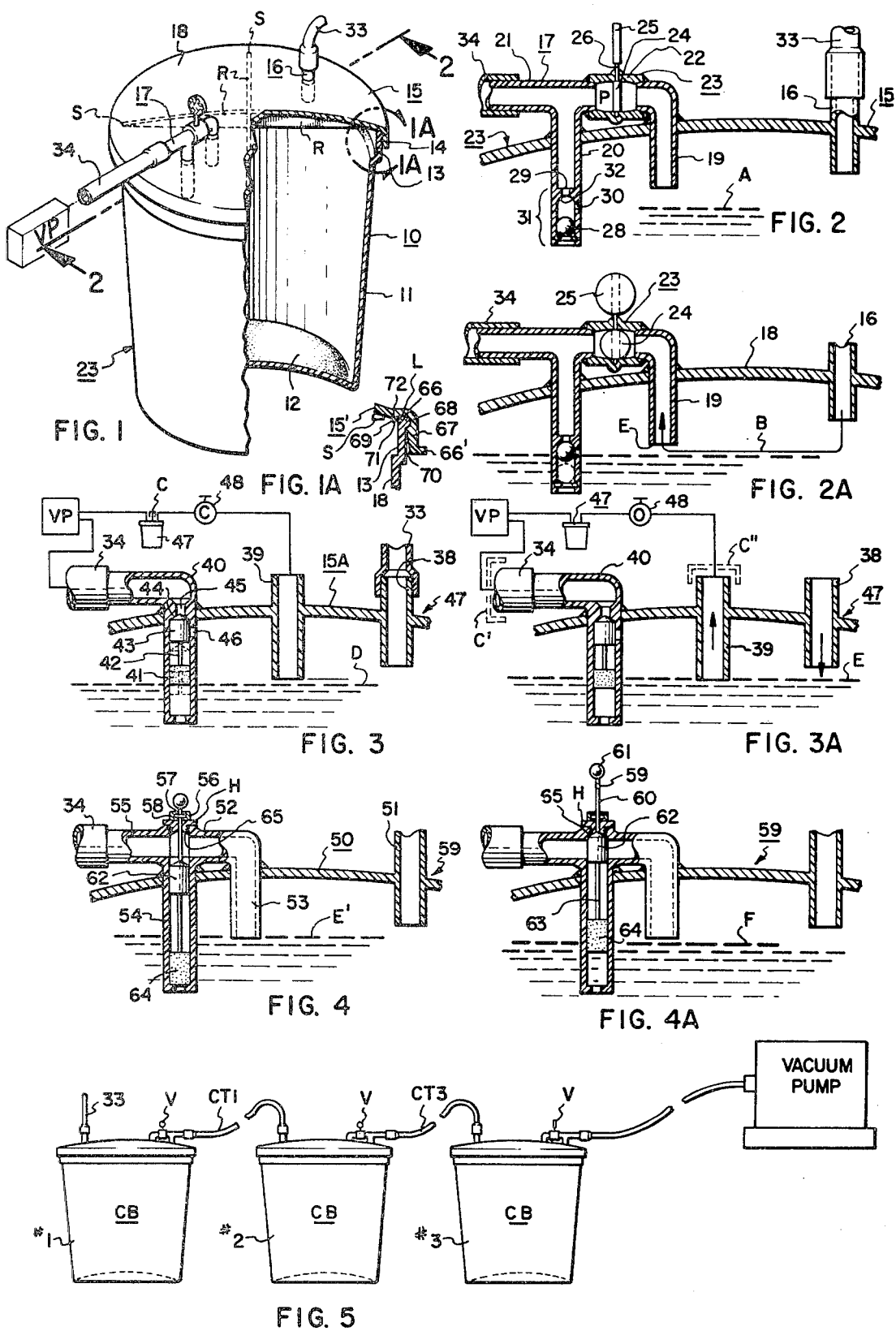

VACUUM-OPERATED FLUID BOTTLE FOR TANDEM SYSTEMS

This is a continuation of application Ser. No. 187,275, filed Oct. 7, 1971, now abandoned, which is a continuation-in-part of Ser. No. 876,438, filed Nov. 13, 1969, now U.S. Pat. No. 3,620,408.

The present invention relates to fluid collection bottles and, more particularly, to a new and improved bottle construction which maximises effective vacuum seal and optimises versatility in use, whether as a single fluid collection bottle or as a bottle insert for a tandem bottle collection system.

There are a number of important features in the present invention and which are advantageous over and an advancement upon prior-art collection bottles. In the first place, the bottle, including as it does a container and a cover, incorporates means built into the container and cover which afford ready attachment of the container in such a manner that a maximum vacuum seal is formed as between the container lip and the cover. This is to be accomplished by virtue of the inclusion of a bead portion in the upper margin of the container and a cover portion receiving the bead such as greater than half of the bead and lip area are contained in a recess of such nature that the mutual fitting provides a long line of seal areas as between the container lip and the cover. In order to effect the same most advantageously, tapered, interior annular surfaces are provided the cover such that the exterior portion of the bead and also the interior edge or margin of the container lip are progressively cammed into place so that the cover will snap over the bead to retain the bead in place within the cover.

Secondly, the invention includes multiple port openings for the cover, one opening being for body fluid reception by way of example, another being for vacuum connection and a possible third being for vacuum connection as well. This is important where tandem systems are contemplated. The second vacuum port may be capped when desired.

Advantageously, there is incorporated into the system suitable valving means for either permitting or, alternatively, automatically shutting-off vacuum connection to the interior of the bottle when a particular fluid level has been achieved. Additionally, the vacuum ports may be connected together in a valving arrangement as hereinafter illustrated such that maximum fluid level is pre-determined in one-container, with addditional fluid automatically being pumped into a second container, or, the second container may be shut off relative to the vacuum communication. A number of possible advantages and techniques are accommodated by the present invention as hereinafter pointed out, through valving both automatic and/or selective.

Additionally, the bottle's vacuum port connected or connectable to a vacuum pump is disposed above the lower extremity of the fluid inlet port so as to aid fluid flow to and/or through the vacuum port while maintaining the spacing of the inlet port above the maximum fluid level in the bottle.

Accordingly, a principal object of the present invention is to provide a new and improved fluid collection bottle and system.

Another object is to provide a vacuum-operated fluid bottle having plural vacuum ports, one having automatic shutoff means, to accommodate automatic fill of successive bottles in a tandem system and, alternatively, automatic shut-off of a single bottle or a selected bottle of a tandem system.

An additional object is to provide a plurality of communication means for covers of vacuum-operated fluid containers.

An additional object is to provide valving means for automatically pre-determining maximum height level of fluid contained within a particular bottle and, in addition, to selectively admit or reject fluid flow of additional fluid entering the bottle into a second fluid container, by way of example.

An additional object is to provide in or for a vacuum system a fluid collection bottle having a vacuum port, connectable to a vacuum pump, and disposed lower than the fluid inlet port thereof.

An additional object of the invention is to provide an improved valving means in a body fluid collection bottle which accommodates a wide variety of uses.

The features of the present invention which are believed to be novel are set forth with particularity in the appended claims. The present invention, both as to its organization and manner of operation, together with further objects and advantages thereof, may best be understood by reference to the following description, taken in connection with the accompanying drawings in which:

FIG. 1 is a perspective view, partially cut away, of a fluid collection bottle constructed in accordance with the principles of the present invention and forming one embodiment thereof.

FIG. 1A is an enlarged detail taken along the line 1A—1A in FIG. 1, illustrating a slight modification of the bottle shown in FIG. 1 and showing a preferred structural arrangement of the engagement of the container of the bottle with its cover or lid.

FIG. 2 is an enlarged fragmentary section taken along the line 2—2 in FIG. 1.

FIG. 2A is a view similar to FIG. 2, but illustrates a control valve as being "open" instead of "closed," as shown in FIG. 2.

FIG. 3 is an enlarged fragmentary section similar to FIG. 2, illustrating another embodiment of the invention so far as container cover construction is concerned.

FIG. 3A is a view similar to FIG. 3 but illustrates the control valve being "open," indicated by the letter O rather than "closed" as indicated by the letter C in FIG. 3.

FIG. 4 illustrates an alternate form of the invention as to the cover or lid thereof; in particular, the FIG. 4 embodiment includes a float valve which is either locked out of engagement with its valve seat or is free to slide to valveclose position as shown in FIG. 4A.

FIG. 4A is a fragmentary view similar to FIG. 4, illustrating that when the valve stem of the embodiment shown in FIGS. 4 and 4A is unlocked, then the valve stem is free to move to allow the valve thereof to seat properly, so as to thereby interrupt vacuum communication with the interior of the bottle; that is done automatically, if desired, through the incorporation of a float in the system.

FIG. 5 is an elevation of a series of fluid collection bottles connected in series or tandem and coupled to a vacuum pump.

In FIG. 1 container 10 includes tapered sidewall 11 and a spherically configured, concavo-convex bottom portion shown here as upwardly convex bottom 12. Also included is an outwardly protruding margin 13 cooperating with depending lip 14 of cover 15. The details of this co-engagement will be described hereafter.

Of special importance in the present invention is the design of a dome-shaped cover 15. In the embodiment of the invention shown in FIG. 1, cover 15 includes tube 16 and tubular member 17. These may be either integral with top portion 18 of cover 15 or may comprise separate parts adhered to the sides of cooperating apertures formed in top portion 18. Thus, tube 16 may comprise simply a tubular boss as illustrated in FIG. 2.

Tubular member 17 includes inverted L-configured tubular portion 19 and tubular valve portion 20. These two are connected to conduit portion 21, tubular valve portion 20 integrally and tubular portion 19 via union 22.

Union 22 may comprise a portion of valve 23 having butterfly valve gate 24 actuated by handle 25; the latter is connected thereto by a stem 26. In the condition shown in FIG. 2, the valve closes the passageway P as between tubular portion 19 and conduit 21.

It is noted that tubular valve portion 20 is of any fluid-rise-responsive valve time such as a cloggable filter or preferably a movable element valve such as the one shown, and may include ball valve 28 which is constructed to serve as a float. Vacuum orifices 29 and 30 are provided in portion 31 of tubular valve portion 20. Also indicated is a valve seat 32 for float valve 28.

Where the fluid bottle 23 of FIG. 1, comprising container 10 and cover 15, is used simply as a single unit in a body fluid collection system, by way of example, then the body fluid hose 33 will be connected to the tube or tubular boss 16 and will be routed to area of the patient upon which surgery is being or has been performed, by way of example.

Hose 34 will be connected to a pressure reduction system such as a vacuum pump VP. When the pump is turned on, then the air will be exhausted out of the interior bottle 23 via apertures 29 and 30. This reduction in pressure will be accompanied by a flow of body fluid through the hose 33 into the interior of the container, as seen in FIG. 2. A rise in the liquid level will ultimately advance float ball 28 upwardly, so that the same will seat against the valve seat 32. The same shuts off air flow through apertures 30 and 29 so that further liquid flow is precluded. Thus, the level A of the fluid is predetermined by the raising of float valve 28.

If several body fluid collection bottles are connected in tandem, in a manner hereinafter explained, such that a subsequent bottle is to be filled upon the filling of the initial bottle 23, then the valve gate 24 will be turned 90° by the handle 25 in a manner illustrated in FIG. 2A. In such event, the reduced pressure or vacuum condition of hose 34 will be translated, as through tube portion 19, such that additional liquid flowing through tube or tubular boss 16 will follow the direction of arrow B, through tubular portion 19 and through the now-open valve to hose 34. During this entire process it will be seen that the ball valve remains seated. Thus, and depending upon the placement of the lower end E of tubular portion 19, the rise in liquid level, owing to the opening of the valve at 24, will not be appreciable.

When the fluid collection bottle 23 of FIG. 2A is again to be used simply as a single fluid collection unit, then the valve 23 will be returned to its closed position, as shown in FIG. 2.

In FIG. 3 alternate cover 15A is indicated. The same is shown to be provided with a body fluid admittance boss 38, tubular vacuum boss 39, and an inverted L-configured tubular member 40. The latter is shown to be provided with a float 41 affixed by stem 42 to valve 43. Valve 43 seats in a valve seat 44 to close passageway communication between opening 45 and opening 46.

Tube 34 is again connected to a vacuum pump. This time, there is a second fluid collection bottle 47 connected through on-off shut-off valve 48 to the tubular boss 39.

Fluid collection bottle 47 of FIG. 3, a cover only on one of the same being shown relative to the detailed fluid level and valve construction, may be constructed such that a third tubular boss may be capped at C as desired. This is illustrated relative to the upper fluid collection bottle 47 shown in schematic diagram form only in FIG. 3.

The operation of the structure shown in FIG. 3 is as follows. Body fluid hose 33 will conduct body fluid through the tubular boss 38 into the interior of the bottle, that is, lower bottle 47. The liquid level rises so as to produce an upward vertical translational movement of the float 41. The same, in being fixedly secured by stem 42 to valve 43, will cause the latter to rise to its seat 44, thereby shutting off vacuum tube communication via apertures 45 and 46 to the interior of the bottle. However, the vacuum generated by the vacuum pump VP in FIG. 3 will be translated through the upper bottle 47 and valve 48, providing the latter is open, such that additional liquid flow, via tubular boss 38 into the interior of the lowermost bottle 47, will be carried upwardly through tubular boss 39 and through 48 into bottle 47. In the upper bottle 47 the tubular boss 39 is capped.

Referring to FIG. 3, if it is desired that solely the lowermost bottle 47 be operative in the blood collection system, then valve 48 in FIG. 3 will be closed, in which event the fluid level will be that determined by the physical characteristics of float 41 when valve 43 is seated. When valve 48 is open, then additional body fluid advancing in the direction E in FIG. 3A, will cause the fluid level to rise slightly in the lowermost bottle 47, with the fluid or liquid advancing upwardly through the now-open valve 48 into the next bottle 47 shown in reduced schematic view.

In FIG. 4, the collection bottle is now supplied with a cover 50 having body fluid receiving boss 51 and tubular unit 52 including inverted L-configured tubular portion 53, valve portion 54 and tubular base portion 55. A locking boss 56 of conventional design may be incorporated in the construction of portion 55. Thus the same may include a slotted opening 57 and an undercut opening 58, the same accommodating pin 59 and stem 60. Stem 60 is provided a ball shaped handle 61, extends to valve 62 and is securely fastened thereto. Valve 62, in turn, is connected by rigid stem 63 to float 64.

The operation of the structure in FIG. 4 is as follows. When the structure is locked in place so that valve 62 is displaced from its seat 65, then the float 64 will not rise with the rising body of liquid within the bottle, but instead will permit the fluid level to fill to a level E'; thereupon, the body liquid will be sucked upwardly through tubular portion 53 and out the hose 34 to the vacuum pump connected thereto, or, the liquid may advance outwardly through hose 34 to another liquid collection bottle connected in tandem to the bottle shown in FIG. 4.

Where the valve in FIG. 4 is unlocked, see FIG. 4A, so that float 64 is effective to advance upwardly and downwardly, then the fluid level within the bottle in FIG. 4A raises the float 64 upwardly so that valve 62 seats at seat 65. This shuts off vacuum communication, in connection with the interior of the fluid collection bottle, so that the fluid level is established at F in FIG. 4A.

The fluid collection bottles connected in tandem or series as indicated in FIG. 5 may individually take the form shown in any of several embodiments such as the fluid collection bottle 23 in FIGS. 1, 2 and 2A, fluid collection bottle 47 in FIGS. 3 and 3A, or the fluid collection bottle 59 in FIGS. 4 and 4A, by way of example. Accordingly, body fluid from the patient will enter at 33 into the fluid collection bottle on the extreme left in FIG. 5, and with the valves V of the fluid collection bottles No. 1 and No. 2 being open and the valve for collection bottle No. 3 in FIG. 5 being closed, fluid will advance upwardly, to the "fill" level in collection bottle No. 1, and, at that level, and since the level of the vacuum port 19 is lower than that of the fluid inlet port 16, will be shunted via collection tube CT1 to collection bottle No. 2. The latter will fill, and then additional body fluid will be pumped by the vacuum pump through collection tube CT3 to collection bottle No. 3. The valve V of collection bottle No. 3 will be closed in the manner illustrated in FIG. 2, for example. Then the last bottle (No. 3) will fill and shut off when full.

If for any given reason any particular body fluid collection bottle No. 1 is chosen to collect fluid only and not to permit additional fluid to pass into a subsequent bottle, then the valve V, corresponding to valve 23 in FIG. 2, may simply be closed. The same likewise is accomplished automatically by the valve construction illustrated in FIG. 4A and in the condition shown in FIG. 4A. Such is accomplished by an automatic rise of float 64. This particular bottle can be removed with its tubing and a new bottle added. Hence, and in fact, any particular bottle may be removed and a new bottle replaced in its system at any given time in the body fluid collection process, this by the appropriate actuation of the valves V in FIG. 5 corresponding to valve 23 in FIG. 2A, 23 in FIG. 3, and valve 62 in FIG. 4A, the latter two of which operate automatically.

An optimum construction in connection with lid securement with the margin 13 of the container 10 is illustrated in FIG. 1A. Margin 13 is shown to include laterally protruding bead portion 66. Cover 15' in FIG. 1A is very slightly modified relative to the cover 15 in FIG. 1. The same includes peripheral flange portion 66' integral with lip 67. Lip 67 includes annular recess 68 and peripheral seat protuberance 69. Inwardly tapered, annular, inner, bead means camming surface 70 is tapered to provide for the easy reception of bead 66 upon insertion of the latter through the tapered interior of the cover, as supplied by tapered surface 70, so that bead 66 will fit in place. Seal protuberance 69 further serves a vacuum seal seat which, with upwardly tapered deformable surface 71 being slightly tapered, will provide a camming action for the 90° interior "corner" 72 of container margin 13 and a surface into which said "corner" will bite upon the application of vacuum.

In operation, when the lid or cover 15' is inserted over container 10, the lid 15, in being formed of slightly resilient plastic, by way of example, will cause the bead 66 to ride up tapered surface 70 until the bead snaps into the bead seat 68. During a latter part of this time the edge 72 will likewise slide down cam surface 69, to provide a seating engagement of the bead 66 with seat 68 and yet provide an effective 3-surface-contact sealing area including not only the bead seat but also the surface 71 and the flat lip area L. When vacuum is applied to the interior of a bottle constructed in accordance with the disclosure of FIG. 1A, a highly effective vacuum seal is created. The bottle construction preferably takes the form shown in FIG. 1, by way of example. This is to say, the lid or cover is spherically, concavo-convexly configured, e.g. dome-shaped, and the bottom 12 is likewise dome-shaped or convex upwardly. When a vacuum of any degree is initially applied to the bottle construction, the dome-shaped character of bottom 12 will not tend to distort as might be the case in the case of a flexible or pliable plastic were the bottom simply horizontal. Correspondingly, as to the cover or lid 15, the compressive strength of the same forms an effective "arch" to counteract atmospheric forces tending to collapse the cover. If desired, stiffener ribs R having rectilinear lower edges, see FIG. 1, may be incorporated in the lid construction as shown in FIG. 1. The outer termination of these ribs should be spaced from the sealing area, particularly at 71 and 72 in FIG. 1A so that the application of vacuum to the bottle will urge the lid downwardly at that area at which the seal to the container becomes effective. Thus, strength of the cover, with its contour, will permit the same to retain its nominal configuration.

Relative to the embodiment shown in FIGS. 3 and 3A, it will be seen that, if so desired, the automatic valve shut-off portion of the cover may be capped, as by a rubber cap C', in lieu of provision the hose 34, and the bottle unit used simply in a tandem or single bottle system such that, when bottle 47 (lowermost) fills, fluid will automatically be routed to tandem bottle 47 (uppermost) by way of example. It is apparent that valve 48 may accordingly be totally eliminated where desired. Optionally, of course, the remaining vacuum conduit may be capped off by rubber cap C''. This will be done with solely a single bottle as used and where the valving portion thereof is effective to provide automatic fluid flow shut-off for this bottle. Thus, and with continuing reference to FIGS. 3 and 3A, either of the vacuum conduits 39, 40 may be capped off, so as to provide for either the automatic successive filling of a series of bottles or for the filling of a single bottle (or the last bottle of a tandem series) having an automatic vacuum shut-off.

Referring to FIGS. 2 and 2A, by way of example, the cross-sectional area of aperture 30 or its equivalent should not be less than that of aperture 29, otherwise evacuation of the bottle might per se inadvertently tend to raise ball 28.

In FIG. 4, a cap H may be used having a self-sealing membrane through which the valve stem 60 passes. In FIG. 4A, ball 61, whether accessible or in an enclosure, may serve as an indicator, indicating that the float has been raised to the pre-determined "fill" fluid level.

Ideal materials used in moulding or otherwise fabricating the cover and container are polyethylene and polystyrene. Where the cover is resilient and flexible, especially at the bead receiving area, then the bead of the container will easily snap into the bead recess area and be sealingly retained in place by the depending flange of the cover.

While particular embodiments of the present invention have been shown and described, it will be obvious to those skilled in the art that changes and modifications may be made without departing from this invention and its broader aspects.

We claim:
1. A vacuum-fillable, liquidcollection bottle having an upper region and a fluid inlet port, and overflow port, a vacuum port at said upper region, said vacuum port being provided with fluid-level operated valve means for automatically shutting off air communication solely through said vacuum port when liquid within said bottle reaches a predetermined level, said overflow port having a depending, liquid-receiving extremity disposed at said predetermined level, said fluid inlet port being disposed above said predetermined level and above said overflow port extremity, and a vacuum pump connected to said vacuum port and selectively coupled to said overflow port, said overflow port being constructed for selective closure and, therefore, selective uncoupling from said vacuum pump.

2. The bottle of claim 1 wherein said fluid inlet and overflow ports each include upstanding, flexible conduit extensions.

3. The bottle of claim 1 wherein said bottle includes valve means operatively interposed between said overflow port and said vacuum pump.

* * * * *